US00PP08487P

United States Patent [19]

Burch

[11] Patent Number: Plant 8,487

[45] Date of Patent: Dec. 7, 1993

[54] VARIEGATED WILD COFFEE PLANT "VARIEGATED WILD COFFEE"

[76] Inventor: James N. Burch, 8006 SW 149th Ave., 380D, Miami, Fla. 33193

[21] Appl. No.: 745,893

[22] Filed: Aug. 16, 1991

[51] Int. Cl.[5] ..... A01H 5/00
[52] U.S. Cl. ..... Plt./51.1
[58] Field of Search ..... Plt./88.1, 54.1, 51.1

[56] References Cited

PUBLICATIONS

Huxley, et al., (Eds.) "Psychotria" *Dictionary of Gardening* 3, 1992 Stockton Press, N.Y., p. 751.

*Primary Examiner*—James R. Feyrer
*Attorney, Agent, or Firm*—William F. Hamrock

[57] ABSTRACT

A new variety of the wild coffee plant known as *Psychotria nervosa* has been asexually propagated. The new plant is characterized by having substantial variegated pigmentation. The new plant may be useful as a drought-tolerant plant for native species landscape in southern Florida.

2 Drawing Sheets

BACKGROUND OF THE INVENTION

This present relates to a new and distinct variety of *Psychotria nervosa* commonly known as the Wild Coffee plant. My new plant is a vegetatively reproduced, unique varietal form of *Psychotria nervosa* and has been named "Variegated Wild Coffee."

Three species of the wild coffee plant (Psychotria: Rubiaceae) inhabit southern Florida. Two of these species (*Psychotria nervosa* and *Psychotria sulzneri*) are common understory plant in the peninsular part of the state. Common wild coffee (*Psychotria nervosa*) is a medium sized shrub or understory plant found in tropical hammock systems in coastal southern Florida, and often in the interior parts of the southern peninsula, in pine and palmetto or oak and cabbage palm habitats. The plant is often found growing in thin, poor soil and in various sunlight regimes. It is a very drought tolerant plant and is cold sensitive. It appears to grow most favorably in coastal areas of the southern part of the Florida peninsula. It is commonly planted as hedge material or as part of other landscape. It produces elliptic, dark green, shiny leaves with prominent lateral veins, hence the species epithet "nervosa".

State and local governments and regulatory agencies in southern Florida emphasize the use of drought tolerant, or water conserving landscape (i.e. "xeriscape"). Some landscape codes may include requirements for xeriscaping and/or the use of native plants as all or part of the planting material. Wild coffee (*Psychotria nervosa*) appears to meet these requirements and is offered for sale by about 50% of the plant dealers registered with the Association of Florida Native Nurseries that occur within the plants' range (Association of Florida Native Nurseries 1986).

I discovered the parent *Psychotria nervosa* plant in Marco Island within an old cultivated area located historically referenced as "Neck Road" north of Barfield Bay (Twp 52, Rng 26, Sec 16), now known as State Road 92. The parent plant that was found is mostly a "wild type" *Psychotria nervosa*, that is, it has mostly normally pigmented leaves except for one branch that has leaves with variegated pigmentation which makes it different from other plants. Variegated individuals have been removed from the parent plant and successfully grown.

ASEXUAL PROPAGATION

Vegative propagation of the variegated forms has been accomplished by air layering method. This is done by removing the stem epidermis, cork (bark), phloem, and cambium meristem layers from the stem, between successive stem node (lateral bud) pairs; the active xylem, inactive xylem, and pith cortex remain intact. Moist humus, or similar material, is then placed around the adjacent acropetal (next higher on the stem) node, and held in place with aluminum foil, plastic, or similar material. The humus must be kept moist, and is maintained surrounding the node for about 2–24 weeks, or until a root system begins to develop from the subject node. When a root mass has developed, the stem may be severed below the node from which the roots originate, the material holding the humus removed, and the basipetal section (root end) of the stem planted in soil. The stem will then grow orthotropically (vertically) to produce a new individual plant with variegated leaves. Asexual clones are identical to the original sport in all distinguishing characteristics.

Other methods of propagation which may be used include the following:

1. Bud grafting of lateral meristematic tissue from variegated leader shoots, to nonvariegated shoots, may also produce true varietal branches, from which individual plants may be derived.

2. Breeding variegated with variegated individual plants or flowering shoots, or breeding variegated with non-variegated individual plants or flowering shoots, may produce a seed stock with the genetic capability to produce a "variegated-type" population.

SUMMARY OF THE NEW VARIETY

The plant of this invention constitutes a color mutant of the wild coffee plant which differs from all those cultured within the State of Florida and which occur in the wild by the following outstanding features:

1. A unique variegation which is stable and characteristically isolated to the leaves of the plant.

2. The variegated plants have produced flowers and seeds; however, none of the seeds has germinated to data. Whether leaf color variegations (or seed viability) are inherited is unknown at this time. No variegations were noted in the inflorescences or fruits produced. Seeds require several weeks (ca. 10–12) to germinate and the subject plants seeds are now being incubated for growth. The trait is currently being tested for heritability.

3. The variegations being of three distinctly different lines: a light green to yellow predominantly marginal color; a dark green predominantly central color, and an intermediate medium green color. Such color variation is believed to be due to the absence of chlorophyll in all, or one or more layers of mesophyll cells within the leaves.

4. A slightly reduced level of vigor when compared to related trees.

5. A reduced water requirement when compared with related trees.

The new and distinct variety, named Variegated Wild Coffee Plant "Variegated Wild Coffee," was not previously known to me.

BRIEF DESCRIPTION OF THE VARIOUS FIGURES OF THE DRAWINGS

The accompanying drawings are color photographs of the subject variety.

The first sheet shows the entire plant.

The second sheet shows a closeup of the variegated leaves.

BOTANICAL DESCRIPTION OF THE PLANT

The botanical details of the new and distinct variety of *Psychotria nervosa* as observed by me grown under general open air horticultural practices in Naples Fla.

Growth Habit

The growth habit of *Psychotria nervosa* is described by Halle et al. (1978) following Leeuwenberg's architectural model, with branching occurring below a terminal inflorescence. However, these specimens commonly produce axillary branches. This is probably induced by environmental conditions, so that trunks or branches are produced by "reiteration" (Halle et al. 1978) to form functional units (branches) that conform to the parent axis' growth strategy.

Branch internode lengths vary from about 0.1 cm to about 10.0 cm., and are usually about 5.0 cm. In direct sunlight, wild *Psychotria nervosa* tend to be compact with smaller leaves and sort internodes (not short shoots). The shrub canopy is irregular and dense in direct sunlight, and is formed mostly by leaves on sympodial replacement shoots. A subcanopy is usually produced by leaves formed on axillary reiteration shoots with longer internodes, resulting in a diffuse subcanopy. Specimens living in shaded environments produce canopies and subcanopies in the same manner, but with longer internodes and larger leaves. The result is a more open or diffuse, irregular canopy and subcanopy. Branch angles of axillary (reiterated) branches on variegated specimens are about 59.6° d(±3.9° S.D.), and those of wild types are about 57.2° (±5.4° S.D.) from their parent axes. Branches forming sympodial replacement shoots on wild types have angles of about 40.8° (±5.8° S.D.) form their parent axes, suggesting a stronger tendency of replacement shoots toward orthotropic growth.

Subject plants have not grown to what is likely to be maximum size: they are expected to be similar to wild type *Psychogtria nervosa.* Scurlock (1987) indicates maximum height of this species at 8' to 10'; The Royal Horticultural Society (1992) indicates maximum height of this species at 2.5 m to 6.0 m.

The subject plant has not been grown in day-long full sunlight; however, it has been grown in a greenhouse with near full sunlight for most or part of the day. In this case the subject plants were grown with wild-type *Psychotria nervosa,* and displayed the same sort of growth reactions to direct sunlight as the wild type. This species usually exists as an understory shrub, and is adapted to diffused light conditions. Its growth is most robust in shaded areas, but it can tolerate some full sun. In higher light conditions, growth tends to be more compact with shorter stem internodes and smaller leaves; leaves become corrugated with corrugations conforming to the pinnate secondary venation. It is probably best considered for areas with some protection from full exposure to sunlight.

This species is known to be used as a house plant, but this is not common. It would probably do well in indoor conditions with full sun part of the day, or moderately high light conditions. Whether air conditioning will adversely affect this species is not known.

The potential use in landscapes for the disclosed plant is probably best considered for areas with some protection from direct sunlight. Such areas may include, but not be limited to, north sides of buildings, partially enclosed atria or patios, screened enclosures, or beneath arborescents.

*Psychotria nervosa* is listed as very drought tolerant (South Florida Water Management District, undated). State and local governments and regulatory agencies in southern Florida now emphasize the use of drought tolerant, or water conserving landscape (i.e., xeriscape). Landscape codes in local ordinances may include requirements for xeriscaping, or the use of native flora as all or part of their planting material (Collier County Ordinance 89-57). In some cases, local ordinances have requirements that land developements perserve appropriate amounts of native habitat; if this is not possible, then the developer may make up the difference of destroyed habitat by planting native species as lansdscape elements (e.g., Collier County Ordinances 89-49, 89–58; Palm Beach County Ordinance 500.35). Similarly, mitigation for destruction of wetlands or other native habitats may be accomplished by habitat reconstruction; often, partly restored, passive recreation areas within developments are allowed. The objective is to offer this variety of shrub as an alternative for the landscape and horticulture market.

*Psychotria nervosa* (wild type) is offered for sale by about 50% of the plant dealers registered with the Association of Florida Native Nurseries, that occur within the plant's range (Association of Florida Native Nurseries 1986). The potential share of the market for this type of plant is not quantified, but it may follow a pattern similar to another native variant, the silver buttonwood (*Conocarpus erectus,* var. sericeus). Silver buttonwood is a back mangrove associated (Tomlinson 1986) that has been successfully marketed as a cultivar for several years, and is commonly used as hedge material or other landscape element.

BOTANICAL DESCRIPTION OF THE PLANT

Growth habit:

*Shape.*—Diffuse, multiple leaders.

*Size.*—8–10 feet high by 3–4 feet wide at maturity. Cold sensitive; leaves and undeveloped stems will not tolerate temperatures below 0° C. Resprouting from mature stems or roots will occur if they have not been frozen.

*Vigor.*—10 inches to 12 inches per year.

*Rooting habit.*—Taproot.

Bark:

*Texture.*—Smooth.

*Thickness.*—1/16–⅛ inch.

*Color.*—New — green. Mature — dark brown. Bark color of the subject plants appears to be the same as the bark color of the wild type *Psychotria nervosa.*

Branches: Branching primarily follows Leeuwenberg's architectural model (Halle et al. 1978), as dichotomously opposing branches form after a terminal infructescence is produced. The infructescence terminates the leader shoot, and allows the development of the opposing axillary buds subtending the infructescence. Usually both buds develop into monopodial branches and grow until they reproduce, sympodially generating two new branches in the same manner. Reproductive activity usually occurs in mid to late summer, but each branch does not necessarily reproduce every season. The timing for reproductive activities of branches is not clearly understood.

Besides the predictable branching that follows reproductive activity, axillary buds frequently develop into adventitious branches by reiteration (Halle et al. 1978). These in turn form branch complexes in the same manner as the parent axes. Also, shoots occasionally develop from subterranean stems or roots; this again appears to be a form of axis reiteration.

Foliage: Variegated.

*Size.*—Length — 2–4 inches. Width — 1–2" inches.

*Petiole.*—Length — about ½ inch. Stipules — interpetiolar.

*Color.*—Leaf colors of the subject plants may be described by comparison with The Royal Horticultural Society Colour Chart as follows: Adaxial surface — Margin area color: R.H.S. Colour Chart #144C. Primary median area color: R.H.S. Colour Chart #146A. Secondary median area color: R.H.S. Colour Chart #141C. Abaxial surface — Margin area color: R.H.S. Colour Chart #145B. Medial area color: R.H.S. Colour Chart #138A.

*Retention.*—About 12 months.

*Psychotria nervosa* produces elliptic leaves with entire margins, acuminate apices, and attenuate to obtuse bases. Leaf adaxial surfaces are glabrous and glossy (Ref. Royal Horticultural Society [1992] for general description of *Psychotria nervosa*). Abaxial surfaces are glauscent and lighter colored than the adaxial surfaces and minutely pubescent around domatia found in vein axils (Tomlinson 1980). Veins are pinnate and prominent (hence the species epitheth "*nervosa*" — Correll and Correll 1982). Leaves are simple and opposite. Stipules are interpetiolar and form a sheath around developing leaves. This sheath is sometimes slightly pubescent, and is shed as the newly formed leaves mature. No variegation or other difference from wild type stipules has been noted in the subject plants.

Leaf color does not change with season. Leaf color may fade with senescence, becoming pale before abscission.

*INFLORESENCE

Dates: Year round, mostly summer.

Flowers:

*Size.*—ca. ⅛–¼ inch across.

*Color.*—White.

*Perfect?.*—Yes.

*Conspicuous?.*—Inflorescence is conspicuous, single flowers are not.

*Self fertile?.*—Not functionally due to structural incompatibility, but are probably self fertile (Tomlinson 1980); self fertilization may be successful with artificial pollination.

* unknown for variegated individuals.

One subject plant has been observed to bloom in the past year. The reproductive organs produced appeared to be the same as those produced by wild type *Psychotria nervosa.* The inflorescence is cymose, producing white flowers about 3 mm wide. Fruits are dark red when mature, about 3.0 mm×5.0 mm. and contain two seeds resembling small coffee beans.

Tomlinson (1980) suggested that this species could be self compatible for pollination and seed production, although the flowers are clearly heterostylous (one of two heterostylar conditions specific to each plant). Attempts at artificial self pollination of the subject plants yielded no seed development. Development of seeds occurred when a subject plant was placed in a wild environment and allowed to accept pollen from other individuals. This suggests that outcrossing is required for fertilization. Breeding experiments will be initiated as soon as opportunity avails, to determine whether differences in leaf color can be considered a heritable trait. It should be noted that, as all adult variegated individuals are clones, there heterostylous nature and presumed self incompatability are probably identical. Therefore, crossing may necessarily be undertaken with $F_2$ wild X variegated progeny. Development to maturity of these plants may require several years; development rates from seed to adult is not known for this species and has not been determined for the subject plants.

*FRUIT

Dates: Year round, mostly summer.

Size: ¼ inch long by 3/16 inch wide.

Shape: Elliptical with longitudinal ridges.

Seed: About 3/16 inch long×⅛ inch wide.

*unknown for variegated individuals.

GENERAL OBSERVATIONS

As a species native to southern Florida, this plant should be well adapted for landscape in this area. It is known to be drought tolerant, well adapted to local soils, and should be resistant to local pests and pathogens. Flowers and seeds have not been produced on variegated individuals up to present time.

The subject plants have been briefly grown in a natural environment, and for that period did not indicate susceptibility to pests or pathogens different from wild type *Psychotria nervosa.*

As a species commonly found in coastal ecosystems, *Psychotria nervosa* probably possesses some tolerance for salt in its surroundings; also, as a drought tolerant species, physiological drought caused by occasional high salinities may not be harmful. Tomlinson (1986) does not indicate this species as a mangrove or mangrove associate, so that sale tolerance may not be high. Tests for salt tolerances of this species are not known to have been performed, and have not been performed for the subject plants: possible tolerances for salt indicated here are speculative.

REFERENCES

Association of Florida Native Nurseries. 1986. Association of Florida Native Nurseries 1986–87 plant and service locator. Association of Florida Native Nurseries, 32 pp.

Correll, D. S. and H. B. Correll. 1982. Flora of the Bahama Archipelago. Ganter and Verlag. 1692 pp.

Halle, F., R. A. A. Oldeman., and P. B. Tomlinson. 1978. Tropical Trees and Forests; An Architectural Analysis. Springer-Verlag, Berlin, 441 pp.

Huxley, A. (ed.). 1992. The New Royal Horticultural Society Dictionary of Gardening. The Royal Horticultural Society. Stockton Press. New York.

Scurlock, J. P. 1987. Native Trees and Shrubs of the Florida Keys. Laurel Press, Pittsburgh, Pa. 220 pp.

South Florida Water Management District. Undated. Xeriscape Plant Guide. South Florida Water Mangement District, West Palm Beach, Fla. 32 pp.

The Royal Horticultural Society, undated. Royal Horticultural Society Colour Chart. The Royal Horticultural Society, London.

Tomlinson, P. B. 1980. The biology of trees native to tropical Florida. Harvard University Printing Office. 480 pp.

Tomlinson, P. B. 1986. The botany of mangroves. Cambridge University Press. 413 pp.

I claim:

1. A new and distinct variegated wild coffee (*Psychotria nervosa*) plant as herein illustrated and described.

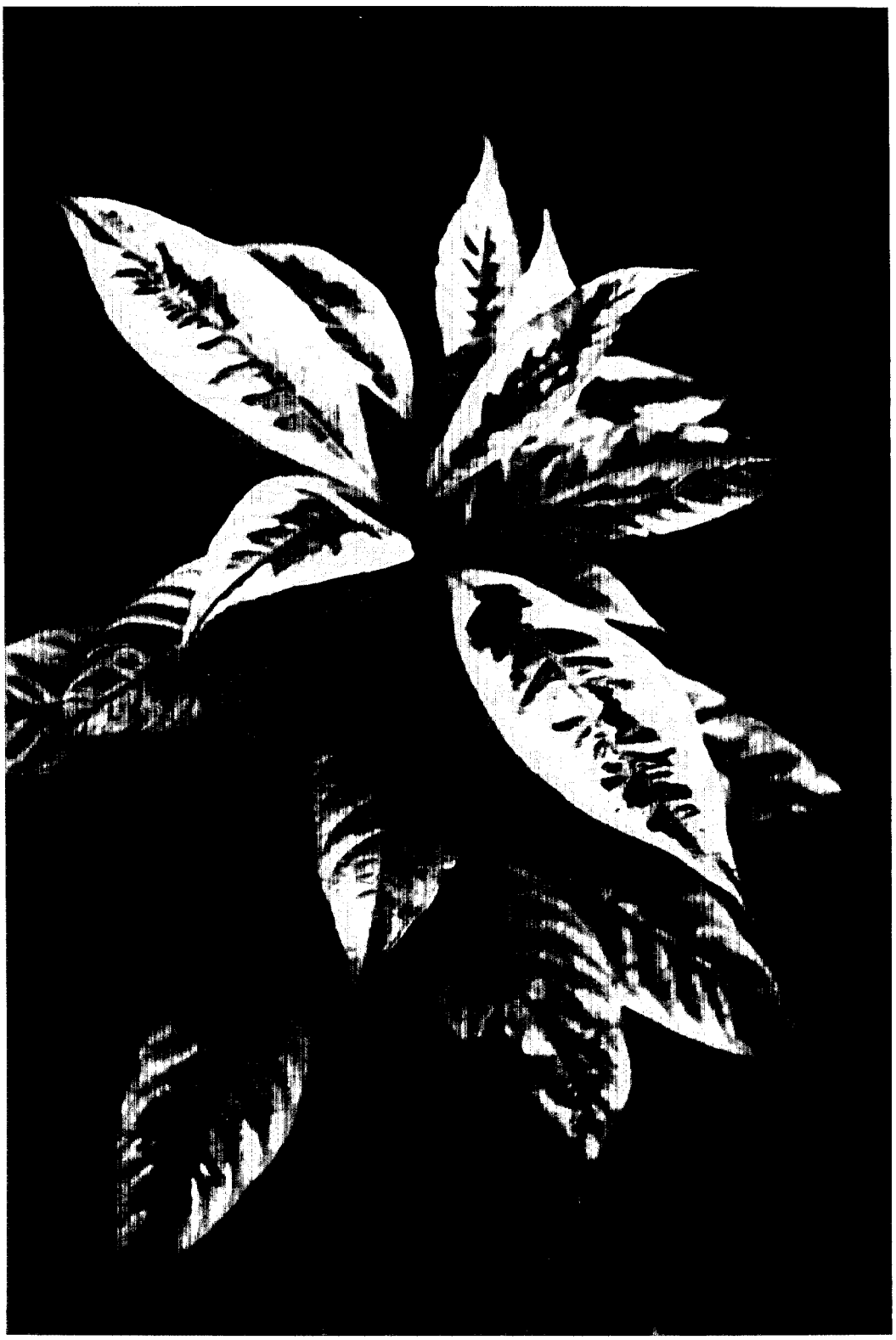

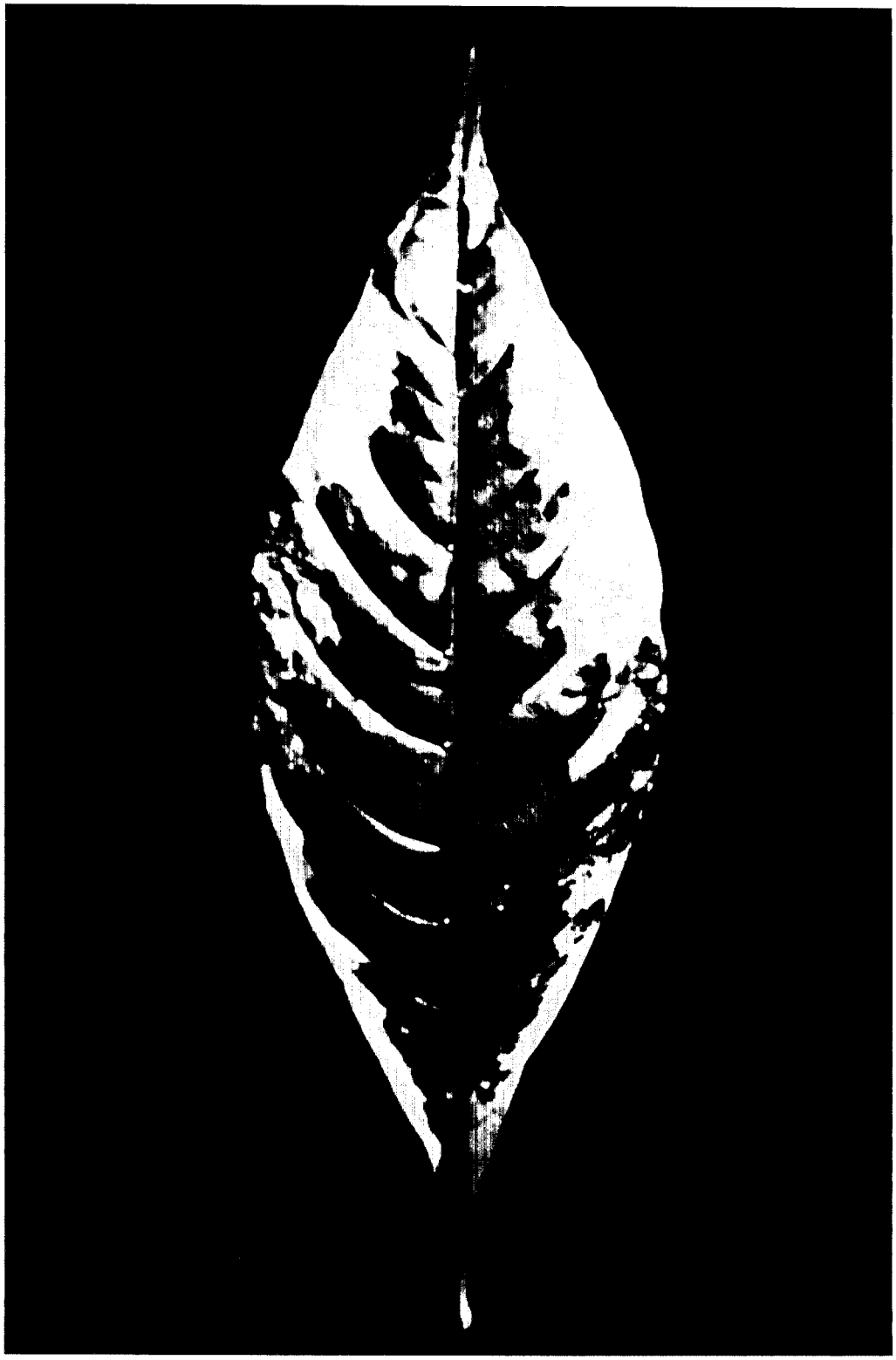

* * * * *